United States Patent
Jacobs et al.

(10) Patent No.: US 7,504,353 B2
(45) Date of Patent: Mar. 17, 2009

(54) HYDROGENATION CATALYSTS

(75) Inventors: Pierre Jacobs, Gooik (BE); François Collignon, La Bruyère (BE); Emmanuel Van Vaerenbergh, Oudenaarde (BE); John Surtees, Jezus-Eik (BE); Anne-Catherine Burteau, Grand-Leez (BE)

(73) Assignee: UCB Pharma, S.A., Brussels (BG)

( * ) Notice: Subject to any disclaimer, the term of this patent is extended or adjusted under 35 U.S.C. 154(b) by 553 days.

(21) Appl. No.: 10/541,531

(22) PCT Filed: Jan. 9, 2004

(86) PCT No.: PCT/EP2004/000107

§ 371 (c)(1),
(2), (4) Date: Mar. 14, 2006

(87) PCT Pub. No.: WO2004/062797

PCT Pub. Date: Jul. 29, 2004

(65) Prior Publication Data

US 2006/0224001 A1     Oct. 5, 2006

(30) Foreign Application Priority Data

Jan. 13, 2003    (EP)  ................... 03000497

(51) Int. Cl.
*B01J 29/70*     (2006.01)
*C07D 207/04*    (2006.01)

(52) U.S. Cl. ..................... 502/150; 548/543
(58) Field of Classification Search .............. 548/543; 502/150

See application file for complete search history.

(56) References Cited

U.S. PATENT DOCUMENTS

| | | | |
|---|---|---|---|
| 5,997,840 A * | 12/1999 | Van Brussel et al. | 423/659 |
| 6,969,770 B2 * | 11/2005 | Surtees et al. | 548/550 |

FOREIGN PATENT DOCUMENTS

| | | |
|---|---|---|
| DE | 198 20 411 A | 1/2000 |
| DE | 199 13 395 A | 9/2000 |
| WO | WO 01/64637 A1 | 9/2001 |
| WO | WO 02/36261 A1 | 5/2002 |

OTHER PUBLICATIONS

De Rege, F. M. et al., "Non-Covalent Immobilization of Homogeneous Cationic Chiral Rhodium-Phosphine Catalyst on Silica Surfaces", *Chemical Communications, Royal Society of Chemistry*, 2000, pp. 1797-1798.

* cited by examiner

*Primary Examiner*—Kamal A Saeed
(74) *Attorney, Agent, or Firm*—McDonnell Boehnen Hulbert & Berghoff LLP

(57) ABSTRACT

A catalyst comprising a chiral transition metal-(1,2-bis(2,5-dialkylphospholano) complex immobilized on a specific zeolitic support useful for the hydrogenation of prochiral substrates.

12 Claims, No Drawings

HYDROGENATION CATALYSTS

The present invention relates to catalysts, which are useful for asymmetric hydrogenation reactions.

Asymmetric hydrogenation is often an essential step in the synthesis of enantiomericaily pure products. Due to the increasing utilisation of pure enantiomers as pharmaceuticals, catalytic hydrogenation reactions of this type have been widely investigated during the last decade.

Both homogeneous and heterogeneous catalysts are suitable for asymmetric reactions. WO 93/01199 describes chiral catalysts based on 1,2-bis(2,5-dialkylphospholano)benzene, also known as "DUPHOS" ligands.

WO 01/64637 describes the use of homogeneous catalysts containing chiral ligands such as DUPHOS for the asymmetric hydrogenation of prochiral alkenes. Those catalysts provide relatively good selectivity and conversion rate, but they can not easily be recovered from the reaction mixture.

WO 02/36261 describes metal-ligand complexes such as metal-DUPHOS immobilised on mesoporous alumino silicates. These heterogeneous catalysts are more easy to handle and to remove from the reaction mixture. However, these catalysts seem to become deactivated relatively rapidly when used several times. Moreover, when used for the hydrogenation of prochiral alkenes, relatively high amounts of catalyst in relation to the prochiral alkene are needed in order to obtain good results, typically in the range of 1:100-5000 (metal: substrate molar ratio).

The present invention overcomes these problems.

The invention relates to a catalyst comprising a chiral transition metal-(1,2-bis(2,5-dialkylphospholano)benzene) complex immobilised on a zeolitic support having a molar ratio $SiO_2/Me_2O_3$ of between 5 and 50, wherein Me designates an element of valence 3 and an external surface area, as developed by pores having a mean diameter higher than 0.8 nm, of at least 90 $m^2/g$.

Zeolites can be described as crystalline, (hydrated) metallosilicates with a framework structure. Their three-dimensional, polyanionic networks are constructed of $SiO_4$ and $MeO_4$ tetrahedra linked through oxygen atoms. Me designates an element of valence 3. The substitution of Si by an element of valence 3 generates a charge imbalance, necessitating the inclusion of a cation.

Zeolites can be represented by the chemical formula $M_{x/n}(MeO_2)_x(SiO_2)_y(H_2O)_z$ where M is the charge compensating cation (such as sodium, potassium, magnesium and calcium), n is the cation valence and z represents the moles of water contained in the zeolitic voids. In general, z is between 0 and 2(x+y).

The preferred zeolites are the aluminosilicates, where Me is aluminium. Many zeolites occur naturally as minerals, but there are also synthetic zeolites, which have the same properties except that in some cases Al and Si have been replaced wholly or in part by other elements such as Ga, Fe, B, Ge or Ti.

Prior art techniques have resulted in the formation of a great variety of synthetic zeolites. These zeolites are designated by a letter, acronym or other convenient symbols, as illustrated by zeolite A, X, Y, L, ZSM-5 and BETA.

Both natural and synthetic zeolites can be used as support in the catalyst according to the present invention.

The zeolites can be used as powder. They can also be transformed via existing technologies into granules, extrudates or pellets. The formed samples usually contain between 0 and 60% binder like silica gel, alumina or clay.

The zeolitic support used in the present invention is preferably chosen between BETA and US-Y topology zeolites, more preferably between BETA zeolites.

BETA zeolites consist of an intergrowth of two distinct structures termed polymorphs A and B. The polymorphs grow as two-dimensional sheets and the sheets randomly alternate between the two. Both polymorphs have a three dimensional network of 12-ring pores. The intergrowth of the polymorphs does not significantly affect the pores in two of the dimensions, but in the direction of the faulting, the pore becomes tortuous, but not blocked. Recently, a pure polymorph C denoted ITQ-17 resulting from the intergrowth of zeolite BETA has been synthesized (A. Corma et al. Chem. Comm. (2001) page 1487 and WO 02/30819).

The US-Y zeolites useable for the catalyst according to the invention are generally US-Y zeolites which are dealuminated via steaming and acid leaching procedures, such as described in DE 199 13 395.

The zeolites used as supports in the catalysts of the present invention preferably have a $SiO_2/Me_2O_3$ molar ratio of at most 40 and most preferably of at most 30. The $SiO_2/Me_2O_3$ molar ratio is preferably of at least 6.

In the present invention, the external surface area ($S_{ext}$) is defined as the surface developed by pores having a mean diameter superior to 0.8 nm (non ultra-micropore volume). $S_{ext}$ is obtained from the treatment of nitrogen adsorption isotherms recorded at 77K according to the procedure described in M. J. Remy, G. Poncelet. *J Phys Chem* 99 773-779, (1995). Particularly suitable zeolitic supports are those having a $S_{ext}$ of at least 200 $m^2/g$.

Particularly suitable zeolitic supports have an ultra-micropore volume of at least 0.08 $cm^3/g$.

The ultra-micropore volume $V_\mu$ is defined herein as the volume developed by pores with diameter smaller than 0.8 nm and can be measured according to the procedure described in M. J. Remy, G. Poncelet. *J Phys Chem* 99 773-779, (1995).

In the catalyst according to the invention, the transition metal is usually selected from rhodium (Rh), ruthenium (Ru), and iridium (Ir). It is preferably Rh or Ru and more preferably Rh.

The alkyl substituent in the 1,2-bis(2,5-dialkylphospholano)benzene (DUPHOS) comprises in general from 1 to 8 carbon atoms and is preferably methyl, ethyl or isopropyl. Most preferred is 1,2-bis(2,5-dimethylphospholano)benzene (Me-DUPHOS). The structure of (S,S)-Me-DUPHOS is shown below:

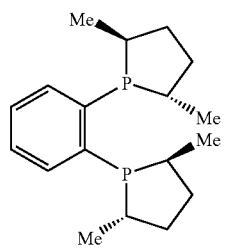

The DUPHOS ligand may be associated to a counterion and/or an olefin.

The counterion is usually selected from halides, $BPh_4(-)$, $ClO_4(-)$, $BF_4(-)$, $PF_6(-)$, $PCl_6(-)$, OAc(-), triflate, mesylate or tosylate. The preferred counterion is $BF_4(-)$.

The olefin is usually selected from ethylene, 1,3-butadiene, benzene, cyclohexadiene, norbornadiene and cycloocta-1,5-diene (COD). Preferred is COD.

The catalysts according to the invention may be prepared by common procedures known to the one skilled in the art, such as described in WO 02/36261. They may be obtained by impregnation of the zeolitic support with a solution of the transition metal-DUPHOS complex. Generally about 1 to 250 µmol DUPHOS, preferably 5 to 10 µmol, is used per g of zeolite.

The catalyst of the present invention is useful for the hydrogenation of unsaturated substrates. The invention catalyst is particularly useful for the production of substantially enantiomerically pure products by hydrogenation of prochiral substrates such as alkenes, ketones, imines and ketimines containing double bonds and in particular for the hydrogenation of functionalised olefines. The solid catalyst is particularly useful for the hydrogenation of compounds of general formula (A) in the form of a Z or an E isomer, such as described in WO 01/64637:

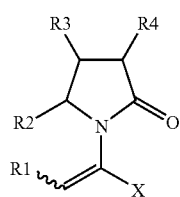

(A)

wherein X is —CONR$^5$R$^6$, —COOR$^7$, —COR$^8$ or —CN;
R$^1$ is hydrogen, alkyl, aryl, heterocycloalkyl, heteroaryl, halogen, nitro, cyano, acyl, ester, amido or carboxy,
R$^2$, R$^3$, R$^4$ are the same or different and each is, independently, hydrogen or halogen, hydroxy, amino, nitro, cyano, acyl, acyloxy, sulfonyl, sulfinyl, alkylamino, carboxy, ester, ether, amido, sulfonic acid, sulfonamide, alkylthio, arylthio, alkyl, alkoxy, oxyester, oxyamido, aryl, arylamino, aryloxy, heterocycloalkyl, heteroaryl, alkenyl;
R$^5$ and R$^6$ are the same or different and each is, independently, hydrogen, hydroxy, alkyl, aryl, heterocycloalkyl, heteroaryl, alkoxy, aryloxy; R$^7$ is hydrogen, alkyl, aryl, heterocycloalkyl or heteroacyl; and
R$^8$ is hydrogen, hydroxy, thiol, halogen, alkyl, aryl, heterocycloalkyl, heteroaryl, alkylthio, arylthio.

The term "alkyl" as used herein, includes saturated monovalent hydrocarbon radicals having straight, branched or cyclic moieties or combinations thereof and contains 1-20 carbon atoms, preferably 1-5 carbon atoms, optionally substituted by 1 to 5 substituents independently selected from the group consisting of halogen, hydroxy, thiol, amino, nitro, cyano, acyl, acyloxy, sulfonyl, sulfinyl, alkylamino, carboxy, ester, ether, amido, sulfonic acid, sulfonamide, alkylthio, arylthio, oxyester, oxyamido, heterocycloalkyl, heteroaryl, (C1-C5)alkoxy, (C6-C10)aryloxy, (C6-C10)aryl.

The term "alkenyl" as used herein, is defined as including branched, unbranched and cyclic unsaturated hydrocarbon radicals having at least one double bond, optionally substituted such as described for alkyl radicals here above.

The term "heterocycloalkyl", as used herein, represents a cyclic alkyl, having at least one O, S and/or N atom interrupting the carbocyclic ring structure such as tetrahydrofuranyl, tetrahydropyranyl, piperidinyl, piperazinyl, morpholino and pyrrolidinyl groups or the same substituted by at least a group selected from halogen, hydroxy, thiol, amino, nitro, cyano.

The term "alkoxy", as used herein includes —O-alkyl groups wherein "alkyl" is defined above.

The term "alkylthio" as used herein, includes —S-alkyl groups wherein "alkyl" is defined above.

The term "alkylamino" as used herein, includes —NHalkyl or —N(alkyl)$_2$ groups wherein "alkyl" is defined above.

The term "aryl" as used herein, includes an organic radical derived from an aromatic hydrocarbon by removal of one hydrogen, such as phenyl or naphthyl, optionally substituted by 1 to 5 substituents independently selected from the group halogen, hydroxy, thiol, amino, nitro, cyano, acyl, acyloxy, sulfonyl, sulfinyl, alkylamino, carboxy, ester, ether, amido, sulfonic acid, sulfonamide, alkylthio, oxyester, oxyamido, aryl, (C1-C6)alkoxy, (C6-C10)aryloxy and (C1-C6)alkyl. The aryl radical generally consists of 1-3 rings, preferably one ring, and contains in general 3-30 carbon atoms, preferably 6-10 carbon atoms.

The term "arylamino" as used herein, includes —NHaryl or —N(aryl)$_2$ groups wherein "aryl" is defined above.

The term "aryloxy", as used herein, includes —O-aryl groups wherein "aryl" is defined as above.

The term "arylthio", as used herein, includes —S-aryl groups wherein "aryl" is defined as above.

The term "heteroaryl", as used herein, unless otherwise indicated, represents an "aryl" as defined above, having at least one O, S and/or N interrupting the carbocyclic ring structure, such as pyridyl, furyl, pyrrolyl, thienyl, isothiazolyl, imidazolyl, benzimidazolyl, tetrazolyl, pyrazinyl, pyrimidyl, quinolyl, isoquinolyl, isobenzofuryl, benzothienyl, pyrazolyl, indolyl, isoindolyl, purinyl, carbazolyl, isoxazolyl, thiazolyl, oxazolyl, benzthiazolyl, or benzoxazolyl, optionally substituted by 1 to 5 substituents independently selected from the group consisting of hydroxy, halogen, thiol, amino, nitro, cyano, acyl, acyloxy, sulfonyl, sulfinyl, alkylamino, carboxy, ester, ether, amido, sulfonic acid, sulfonamide, alkylsulfonyl, alkoxycarbonyl, oxyester, oxyamido, alkoxycarbonyl, (C1-C5)alkoxy, and (C1-C5)alkyl.

The term "arylalkyl" as used herein represents a group of the formula aryl-(C1-C4 alkyl)-.

The term "acyl" as used herein, represents a group of formula alkyl-CO—, aryl-CO—, heteroaryl-CO— or arylalkyl-CO—, wherein the various hydrocarbon radicals are as defined in this section.

The term "acyloxy" as used herein, represents a group of formula alkyl-CO—O—, aryl-CO—O—, heteroaryl-CO—O— or arylalkyl-CO—O—, wherein the various hydrocarbon radicals are as defined in this section.

The term "sulfonyl" represents a group of the formula —SO$_2$-alkyl or —SO$_2$-aryl wherein "alkyl" and "aryl" are defined above.

The term "sulfinyl" represents a group of the formula —SO-alkyl or —SO-aryl wherein "alkyl" and "aryl" are defined above.

The term "sulfonamide" represents a group of formula —SO$_2$NH$_2$.

The term "ester" means a group of formula —COO-alkyl, or —COO-aryl wherein "alkyl" and "aryl" are defined above.

The term "oxyester" means a group of formula —O—COO-alkyl, or —O—COO-aryl wherein "alkyl" and "aryl" are defined above.

The term "ether" means a group of formula alkyl-O-alkyl or alkyl-O-aryl or aryl-O-aryl wherein "alkyl" and "aryl" are defined above.

The term "amido" means a group of formula —CONRR' wherein R and R' are independently selected from hydrogen, "alkyl" or "aryl".

The term "oxyamido" means a group of formula —O—CONRR' wherein R and R' are independently selected from hydrogen, "alkyl" or "aryl".

The catalyst is particularly suitable for the hydrogenation of substrates of formula (A) wherein $R^1$ is alkyl, $R^2$ and $R^4$ are hydrogen, $R^3$ is H, optionally halogenated alkyl or alkenyl and X is —$CONH_2$, —COOMe, —COOEt or —COOH and more particularly for the hydrogenation of methyl or ethyl (Z,E)-2-(2-oxotetrahydro-1H-1-pyrrolyl)-2-butenoate.

The invention therefore further relates to a process for the hydrogenation of unsaturated substrates such as described above wherein a catalyst according to the invention is used.

The temperature at which the process is conducted is generally comprised between 0 and 65° C., preferably between 15 and 30° C. The reaction is usually performed under hydrogen pressure in the range of 1 to 50 bar and preferably at 2 to 6 bar. In general, the amount of catalyst used in the process according to the invention is such that the substrate:catalyst (transition metal) molar ratios are in the range of 20 to 50000:1. The substrate:catalyst ratio is preferably superior to 1000, most preferably superior to 5000.

Usually the hydrogenation reactions with the catalyst according to the present invention are performed in the presence of a suitable solvent. Preferred solvents are selected from ethers, alcohols or mixtures thereof. More preferably the solvent is a mixture of ether and alcohol, particularly in a volume ratio 2:1. The most preferred solvent is diisopropyl ether and its mixture with methanol.

The use of ethers or mixtures of ethers with alcohols permits to have a particularly low degree of metal leaching.

The process according to the invention permits to obtain a high conversion, usually superior to 95% and a high conversion rate. Surprisingly it has been found that the conversion is as rapid or can even be more rapid than with a homogeneous catalyst. The process according to the invention permits to obtain a high selectivity. The catalyst according to the invention presents a high activity, so that very high substrate:catalyst ratios can be used. The catalyst presents a high activity at substrate:catalyst ratios higher than 5000, even higher than 10000 or 15000. Hence, the contamination of the final products with catalyst residues, especially with the transition-metal, is low. This also reduces the cost of the final product. Moreover the catalyst according to the invention permits an easy recovery and reuse, which is ecologically and economically very advantageous.

The invention is further illustrated by the following examples. The results are summarised in Table 1 and Table 2.

EXAMPLE 1

Asymmetric hydrogenation of Methyl (Z,E)-2-(2oxotetrahydro-1H-1-pyrrolyl)-2-butenoate with [Rh-(S,S-MeDUPHOS)(COD)$BF_4$—] immobilised on BETA zeolite In a nitrogen atmosphere, 0.0129 g [Rh-(S,S-MeDUPHOS)(COD)$BF_4$—] was dissolved in degassed 6 ml methanol. The yellow solution was added to 3 g of an acid zeolite BETA provided by Uetikon in extrudate form (sample PB/65H). The impregnated solid was dried for 1 hour under vacuum.

Dry yellowish extrudates were obtained and stored in a nitrogen atmosphere.

A mixture of Z and E-isomers of Methyl-2-(2 oxotetrahydro-1H-1-pyrrolyl)-2-butenoate (9.98 g) and 26.51 g of methanol were weighted into a 200 ml flask. The reaction mixture was degassed (3×vacuum/nitrogen). The flask and a 50 ml AutoclaveFrance reactor were placed in a plastic glove box which was then purged by five vacuum/nitrogen cycles. The reactor was filled with 33.14 g of the degassed mixture and 1.1153 g of the dried catalyst. The substrate:catalyst molar ratio was 6795. The reactor was then pressurised with hydrogen to an initial pressure of 4.8 bar and then released to a pressure of 1 bar. This operation was repeated three times. Finally the reaction mixture was left to stir at room temperature at a constant hydrogen pressure of 4.8 bar.

Reaction samples were collected after 2 and 14 hours.

The products were analysed by chiral gas chromatography (using a HP 6890 equipped with a FI detector and a Chirasil-DexCB fused silica column) and atomic absorption spectroscopy (at 343.5 nm with a Varion Techtron AA6).

The conversion, turn-over frequency C(OF) and enantiomeric excess (% ee) are shown in Table 1.

The conversion is defined as [number of moles substrate converted/initial number of moles substrate in the reaction mixture]×100.

The TOF is defined as (number of moles substrate converted/number of moles DUPHOS)/time.

The enantiomeric excess is defined by the relative excess of one enantiomer to the other (% ee of S=([S]−[R])/[R]+[S])×100), in which [R] and [S] stand for the concentrations of both enantiomers in the reaction mixture).

EXAMPLE 2

Example 1 was reproduced except that diisopropylether was used as solvent. The reaction conditions and results are shown in Table 1.

EXAMPLE 3

Example 1 was reproduced except that a mixture of methanol and diisopropylether in a volume ratio 1:2 was used as solvent. The reaction conditions and results are shown in Table 1.

EXAMPLE 4

Example 1 was reproduced except that a mixture of methanol and diethylether in a volume ratio 1:2 was used as solvent. The results are shown in Table 1.

COMPARATIVE EXAMPLE 5R

Example 1 was reproduced except that non-supported Rh-(S,S-MeDUPHOS)(COD)$BF_4$— was used as catalyst. The results are shown in Table 1.

COMPARATIVE EXAMPLE 6R

Example 1 was reproduced except that the catalyst was supported on mesoporous alumino silicate Al-MCM-41 synthesized according to the procedure of Yu et al. (J. Yu, J. L. Shi, L. Z. Wang, M. L. Ruan, D. S. Yan, *Ceramics International* 26:(4) 359-362 (2000)). The results are shown in Table 1.

EXAMPLE 7

Example 1 was reproduced except that the catalyst was supported on a US-Y zeolite (CBV 720) from Zeolyst. The properties of the zeolite and the results are shown in Table 1.

COMPARATIVE EXAMPLE 8R

Example 1 was reproduced except that the catalyst was supported on a US-Y zeolite from Zeolyst (CBV 760). This zeolitic support had a $SiO_2/Al_2O_3$ ratio outside the scope of the invention. The properties of the zeolite and the results are shown in Table 1.

COMPARATIVE EXAMPLE 9R

Example 1 was reproduced except that the catalyst was supported on a US-Y zeolite from Zeolyst (CBV 600) having an external surface area outside the scope of the invention. The properties of the zeolite and the results are shown in Table 1.

EXAMPLE 10

Example 1 was reproduced except that the catalyst was supported on a ZSM-5 zeolite. The properties of the zeolite and the results are shown in Table 1.

TABLE 1

| Ex n° | Support | $SiO_2/Al_2O_3$ (1) | Sext ($m^2/g$) (2) | Vμ (ml/g) (3) | Solvent | S/C | Time (h) | Conv. (%) | TOF ($h^{-1}$) | ee (%) |
|---|---|---|---|---|---|---|---|---|---|---|
| 1 | Zeolite BETA | 19.8 | 226 | 0.19 | MeOH | 6795 | 2.25 | 6.3 | 191.3 | 93.1 |
|   |   |   |   |   |   |   | 14.5 | 100.0 | 468.6 | 98.5 |
| 2 | Zeolite BETA | 19.8 | 226 | 0.19 | DIPE | 5556 | 20 | 98.1 | 283.6 | 99.2 |
| 3 | Zeolite BETA | 19.8 | 226 | 0.19 | MeOH/DIPE | 5882 | 15 | 100.0 | 376.3 | 99.2 |
| 4 | Zeolite BETA | 19.8 | 226 | 0.19 | MeOH/$Et_2O$ | 6250 | 22 | 99.6 | 283.9 | 98.2 |
| 5R | — | — | — | — | MeOH | 5882 | 48 | 98.1 | 119.1 | 96.2 |
| 6R | Al-MCM-41 | 20 | 610 | — | MeOH | 7143 | 19 | 12.5 | 47.1 | 95.8 |
|   |   |   |   |   |   |   | 43 | 25.1 | 41.3 | 95.5 |
|   |   |   |   |   |   |   | 163 | 86.1 | 36.9 | 94.6 |
| 7 | Zeolite US-Y | 26.0 | 103 | 0.27 | MeOH | 6250 | 18 | 68.7 | 242.7 | 97.1 |
|   |   |   |   |   |   |   | 43 | 91.5 | 134.2 | 97.3 |
| 8R | Zeolite US-Y | 60.0 | 143 | 0.25 | MeOH | 5263 | 112 | 88.0 | 40.5 | 95.4 |
| 9R | Zeolite US-Y | 5.6 | 51 | 0.24 | MeOH | 7143 | 139 | 95.7 | 50.4 | 94.0 |
| 10 | Zeolite ZSM-5 | 50 | 112 | 0.14 | MeOH | 5882 | 17 | 49.7 | 171.0 | 96.4 |
|   |   |   |   |   |   |   | 48 | 97.2 | 118.5 | 96.7 |

((1), (2) and (3): values corresponding to the pure zeolite).

Table 1 shows that the catalyst according to the invention permits to obtain a higher conversion rate in comparison with DUPHOS supported on supports having properties outside of the scope of this invention.

EXAMPLE 11

Example 1 was reproduced except that dimethyl itaconate was used as substrate and a zeolite BETA supplied from Zeolyst (in powder form) was used.

The reaction conditions and results are shown in Table 2.

EXAMPLE 12

Example 11 was reproduced except that diisopropylether was used as solvent. The reaction conditions and results are shown in Table 2.

COMPARATIVE EXAMPLE 13R

Example 12 was reproduced except that a catalyst supported on a mesoporous alumino silicate Al-MCM-41 support having the properties described in Table 2 was used instead of the invention catalyst. The results are shown in Table 2.

TABLE 2

| Ex n° | Support | SiO$_2$/Al$_2$O$_3$ | Sext (m$^2$/g) | Vµ (ml/g) | Solvent | S/C (%) | Time (h) | Conversion (%) | TOF (h$^{-1}$) | ee (%) |
|---|---|---|---|---|---|---|---|---|---|---|
| 11 | Zeolite BETA | 26 | 192 | 0.19 | MeOH | 3984 | 1.0 | 74.7 | 2974 | 97.6 |
|    |              |    |     |      |      |      | 2.1 | 99.0 | 1894 | 97.4 |
| 12 | Zeolite BETA | 26 | 192 | 0.19 | DIPE | 17152 | 1.3 | 15.0 | 1932.4 | 100.0 |
|    |              |    |     |      |      |       | 17.3 | 83.1 | 821.9 | 98.1 |
| 13R | Al-MCM-41 | 20 | 610 | — | DIPE | 18517 | 1.3 | 0.7 | 96.2 | 100.0 |
|    |           |    |     |   |      |       | 18.7 | 4.7 | 46.8 | 91.3 |

Comparison of example 12 with comparative example 13R shows that the catalyst according to the invention permits to obtain high conversion rates, even at substrate:catalyst ratios exceeding 15000.

The invention claimed is:

1. A catalyst comprising a chiral transition metal-(1,2-bis (2,5-dialkylphospholano)benzene) complex immobilised on a zeolitic support having
   a molar ratio SiO$_2$/Me$_2$O$_3$ of between 5 and 50 wherein Me designates an element of valence 3 and
   an external surface area, as developed by pores having a mean diameter higher than 0.8 nm, of at least 90 m$^2$/g.

2. The catalyst as claimed in claim 1, having an ultra-micropore volume of at least 0.08 cm$^3$/g.

3. The catalyst as claimed in claims 1, wherein the support is a BETA topology zeolite.

4. The catalyst as claimed in claims 1, wherein the zeolitic support has a molar ratio SiO$_2$/Me$_2$O$_3$ of at most 30.

5. The catalyst as claimed in claims 1, wherein Me is Al.

6. The catalyst as claimed in claims 1, wherein the transition metal is Rh.

7. A process of hydrogenation of a prochiral substrates comprising contacting the prochiral substrate with a hydrogenating agent and a catalyst according to claims 1.

8. The process as claimed in claim 7, wherein the substrates are functionalised olefines.

9. The process as claimed in claim 8, wherein the substrate is a compound of general formula (A)

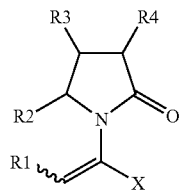

(A)

wherein

X is —CONR$^5$R$^6$, —COOR$^7$, —CoR$^8$ or —CN;

R$^1$ is hydrogen, alkyl, aryl, heterocycloalkyl, heteroaryl, halogen, nitro, cyano, acyl, ester, amido or carboxy;

R$^2$, R$^3$, R$^4$ are the same or different and each is, independently, hydrogen, halogen, hydroxy, amino, nitro, cyano, acyl, acyloxy, sulfonyl, sulfinyl, alkylamino, carboxy, ester, ether, amido, sulfonic acid, sulfonamide, alkylthio, arylthio, alkyl, alkoxy, oxyester, oxyamido, aryl, arylamino, aryloxy, heterocycloalkyl, heteroaryl or alkenyl;

R$^5$ and R$^6$ are the same or different and each is, independently, hydrogen, hydroxy, alkyl, aryl, heterocycloalkyl, heteroaryl, alkoxy, aryloxy; R$^7$ is hydrogen, alkyl, aryl, heterocycloalkyl or heteroacyl; and R$^8$ is hydrogen, hydroxy, thiol, halogen, alkyl, aryl, heterocycloalkyl, heteroaryl, alkylthio, arylthio.

10. The process as claimed in claim 9, wherein the substrate is methyl (Z,E)-2-(2 oxotetrahydro-1H-1-pyrrolyl)-2-butenoate.

11. The process as claimed in claims 7 carried out in a solvent selected from ethers, alcohols and their mixtures.

12. The process as claimed in claim 11, wherein the solvent is diisopropyl ether or its mixture with methanol.

* * * * *